US009709519B2

(12) United States Patent
Harding et al.

(10) Patent No.: US 9,709,519 B2
(45) Date of Patent: *Jul. 18, 2017

(54) MEASURING DEVICE AND METHODS FOR USE THEREWITH

(71) Applicant: AGAMATRIX, INC., Salem, NH (US)

(72) Inventors: Ian Harding, Wells (GB); Sridhar G. Iyengar, Salem, NH (US); Baoguo Wei, Salem, NH (US); Steven Diamond, San Mateo, CA (US); Martin Forest, Nashua, NH (US)

(73) Assignee: AgaMatrix, Inc., Salem, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/816,786

(22) Filed: Aug. 3, 2015

(65) Prior Publication Data

US 2016/0033441 A1 Feb. 4, 2016

Related U.S. Application Data

(63) Continuation of application No. 14/088,993, filed on Nov. 25, 2013, now Pat. No. 9,097,651, which is a continuation of application No. 13/108,621, filed on May 16, 2011, now Pat. No. 8,591,815, which is a continuation of application No. 10/907,790, filed on Apr. 15, 2005, now Pat. No. 7,964,146.

(60) Provisional application No. 60/594,285, filed on Mar. 25, 2005, provisional application No. 60/521,592, filed on May 30, 2004.

(51) Int. Cl.
*G01N 33/49* (2006.01)
*G01N 27/403* (2006.01)
*G01N 27/28* (2006.01)
G01N 27/327 (2006.01)
G01N 33/50 (2006.01)

(52) U.S. Cl.
CPC ......... *G01N 27/28* (2013.01); *G01N 27/3272* (2013.01); *G01N 27/3273* (2013.01); *G01N 27/403* (2013.01); G01N 27/3271 (2013.01); G01N 33/50 (2013.01)

(58) Field of Classification Search
CPC .. G01N 27/28; G01N 27/3272; G01N 27/403; G01N 27/3273
See application file for complete search history.

(56) References Cited

U.S. PATENT DOCUMENTS

| 3,646,814 | A | 3/1972 | Christoph et al. |
|---|---|---|---|
| 4,752,740 | A | 6/1988 | Steininger |
| 4,798,655 | A | 1/1989 | Diamond |
| 5,108,564 | A | 4/1992 | Szuminsky et al. |
| 5,124,661 | A | 6/1992 | Zelin et al. |
| 5,507,288 | A | 4/1996 | Bocker et al. |
| 5,540,828 | A | 7/1996 | Yacynych |
| 6,251,260 | B1 | 6/2001 | Heller et al. |
| 6,391,558 | B1 | 5/2002 | Henkens et al. |
| 6,933,153 | B1 | 8/2005 | Mattiasson et al. |
| 7,964,146 | B2 * | 6/2011 | Harding ............. G01N 27/3273 205/400 |
| 8,591,815 | B2 * | 11/2013 | Harding ............. G01N 27/3273 204/403.01 |
| 8,852,510 | B2 * | 10/2014 | Harding ............. G01N 27/3273 204/403.02 |
| 2003/0064525 | A1 | 4/2003 | Liess |
| 2003/0178322 | A1 | 9/2003 | Iyengar et al. |
| 2004/0146863 | A1 | 7/2004 | Pisharody et al. |
| 2005/0054082 | A1 | 3/2005 | Pachl et al. |
| 2005/0069892 | A1 | 3/2005 | Iyengar et al. |
| 2007/0000778 | A1 | 1/2007 | Hsiung et al. |

FOREIGN PATENT DOCUMENTS

| DE | 4100727 A1 | 7/1992 |
|---|---|---|
| JP | 11235196 | 8/1999 |
| SU | 978027 | 11/1982 |
| WO | 02053024 A2 | 7/2002 |
| WO | 02077633 A1 | 10/2002 |
| WO | 03046538 A1 | 6/2003 |
| WO | 03056314 A2 | 7/2003 |
| WO | 03060154 A2 | 7/2003 |
| WO | 03069304 A2 | 8/2003 |
| WO | 2005022143 A2 | 8/2004 |

OTHER PUBLICATIONS

Roth et al., Characterization of charge storage in redox-active self-assembled monolayers, Langmuir, 2002, pp. 4030-4040, vol. 18, No. 10, XP002951267, USSBL 0743-7463.

* cited by examiner

*Primary Examiner* — Paul Hyun
(74) *Attorney, Agent, or Firm* — Larson & Anderson, LLC

(57) ABSTRACT

The ability to switch at will between amperometric measurements and potentiometric measurements provides great flexibility in performing analyses of unknowns. Apparatus and methods can provide such switching to collect data from an electrochemical cell. The cell may contain a reagent disposed to measure glucose in human blood.

15 Claims, 10 Drawing Sheets

US 9,709,519 B2

MEASURING DEVICE AND METHODS FOR USE THEREWITH

CROSS-REFERENCE TO RELATED APPLICATIONS

This application claims priority from U.S. application Ser. No. 60/521,592 filed May 30, 2004, and from U.S. application Ser. No. 60/594,285 filed Mar. 25, 2005, each of which is incorporated herein by reference for all purposes.

BACKGROUND

Electrochemical reactions may be used to measure quantities and concentrations in solutions.

FIG. 1 is a schematic diagram of an electrochemical interface apparatus, also known as a potentiostat, for a standard three-electrode configuration. Electrochemical cell 39 has a reference electrode 37, a counter electrode 36, and a working electrode 38. The cell 39 contains a substance being analyzed as well as a reagent selected for its utility. The reagent forms part of an electrochemical reaction. It will be appreciated that there are other circuits that can accomplish the functions described here, and that this is only one embodiment thereof.

A voltage is applied to the cell at 36, based upon a voltage input provided at input 34. This voltage at 34 is defined relative to a ground potential 40. In some embodiments this is a known voltage. More generally, in a three-electrode system, the voltage at 36 assumes whatever value is needed to make sure that the potential difference between 37 and 38 is substantially equal to the potential difference between 34 and 40.

Amplifier 35, preferably an operational amplifier, is used to provide gain as needed and to provide isolation between the input 34 and the electrodes 36 and 37. In the arrangement of FIG. 1 the gain is a unity voltage gain and the chief function of the amplifier 35 is to provide a high-impedance input at 34 and to provide sufficient drive to work with whatever impedance is encountered at electrode 36.

As the electrochemical reaction goes forward, current flows. Working electrode 38 carries such current. A selector 31 selects a resistor from a resistor bank 30, to select a current range for measurement of this current. Amplifier 32, preferably an operational amplifier, forms part of a circuit by which an output voltage at 33 is indicative of the current through the electrode 38. The output voltage at 33 is proportional to the product of the current at 38 and the selected resistor.

In one example, blood such as human blood is introduced into the cell. A reagent in the cell contributes to a chemical reaction involving blood glucose. A constant and known voltage at 34 is maintained. The output voltage at 33 is logged and the logged data are analyzed to arrive at a measurement of the total current that flowed during a defined measurement interval. (Typically this interval is such that the reaction is carried out to completion, although in some embodiments the desired measurements may be made without a need for the reaction to be carried out to completion.) In this way the glucose level in the blood may be measured.

As will be discussed below, the input at 34 may preferably be other than constant. For example it may be preferable that the input at 34 be a waveform selected to optimize certain measurements. The analog output of a digital to analog converter may be desirably connected at input 34, for example.

The measurement just described may be termed an "amperometric" measurement, a term chosen to connote that current through the reaction cell is what is being measured.

In some measurement situations it is possible to combine the counter electrode and the reference electrode as shown in FIG. 2, into a single electrode 41.

One example of a prior art circuit is that shown in German patent application DE 41 00 727 A1 published Jul. 16, 1992 and entitled "Analytisches Verfahren für Enzymelektrodensensoren." That circuit, however, does not, apparently, perform an amperometric measurement upon the reaction cell. That circuit appears to perform voltage readings, and an integrated function of voltage, with respect to a reference electrode of a cell (relative to a working electrode of the cell) and not with respect to a counter electrode (relative to the working electrode of the cell).

In this circuit the measured potential is a function of (among other things) the concentration of an analyte. Stating the same point in different terms, this circuit does not and cannot yield a signal that is independent of concentration of the analyte.

SUMMARY OF THE INVENTION

FIG. 3 shows an improvement upon the previously described apparatus. In FIG. 3, an ideal voltmeter 42 is provided which can measure the potential across the electrodes 41, 38. Switch 44 is provided which is opened when the potential is to be measured. In this way the cell 39 is "floating" as to at least one of its electrodes, permitting a voltage measurement that is unaffected by signals at the amplifier 35.

The switch 44 may be a mechanical switch (e.g. a relay) or an FET (field-effect transistor) switch, or a solid-state switch. In a simple case the switch opens to an open circuit; more generally it could open to a very high resistance.

The ability to switch at will between amperometric measurements and potentiometric measurements provides great flexibility in performing analyses of unknowns. The various potential benefits of this approach are discussed in some detail in co-pending U.S. application Ser. No. 10/924,510, filed Aug. 23, 2004 and incorporated herein by reference for all purposes. Measurement approaches are discussed in some detail in U.S. application Ser. No. 10/907,815, filed Apr. 15, 2005, and in U.S. application Ser. No. 10/907,813, filed Apr. 15, 2005, each of which is incorporated by reference for all purposes.

DESCRIPTION OF THE DRAWING

The invention will be described with respect to a drawing in several figures.

DETAILED DESCRIPTION

Variations upon the topology will now be described.

Figure 3:
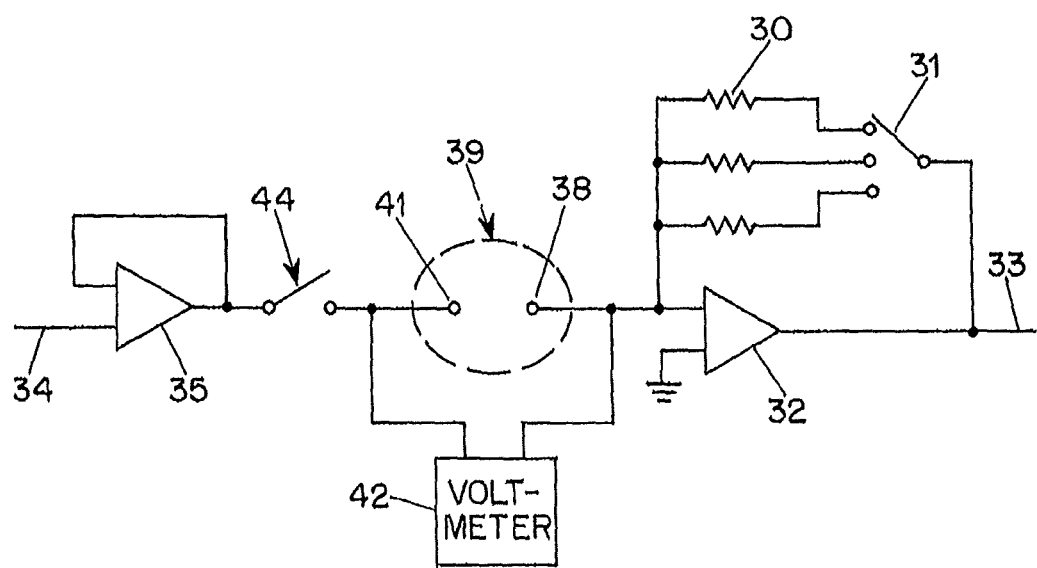
FIG. 3 shows an improvement upon the previously described apparatus according to the invention
Figure 4A:
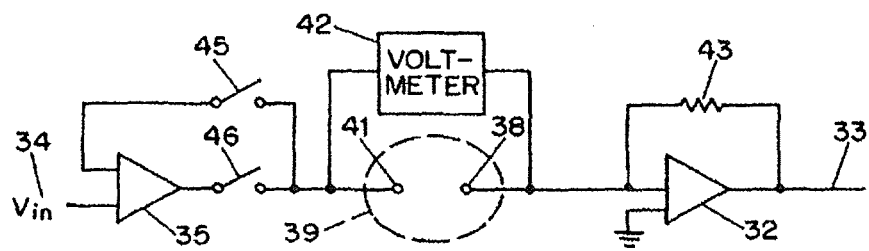
FIGS. 4a and 4b show embodiments in which two switches are used rather than the single switch of FIG. 3.
Figure 4B:
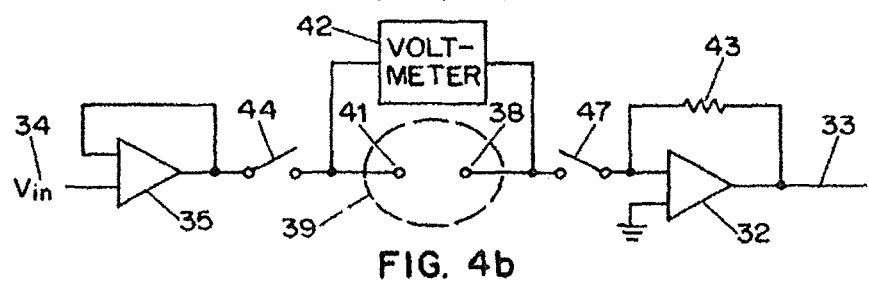

FIGS. 4a and 4b show embodiments in which two switches are used rather than the single switch of FIG. 3. In each embodiment, two switches are opened to isolate the cell for purposes of voltage measurement by means of voltmeter 42.

In FIG. 4a, switches 45, 46 are opened to isolate the two-electrode cell 39 from the output of amplifier 35 and from the feedback path to the inverting input of amplifier 35.

In FIG. 4b, switches 44, 47 are opened to isolate the two-electrode cell 39 at both the electrode 41 and the electrode 38.

Figure 4C:
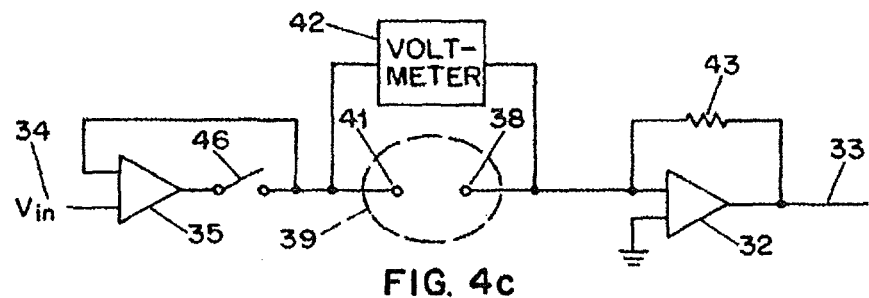
FIGS. 4c and 4d show embodiments in which one switch is used to effect the isolation.
Figure 4D:
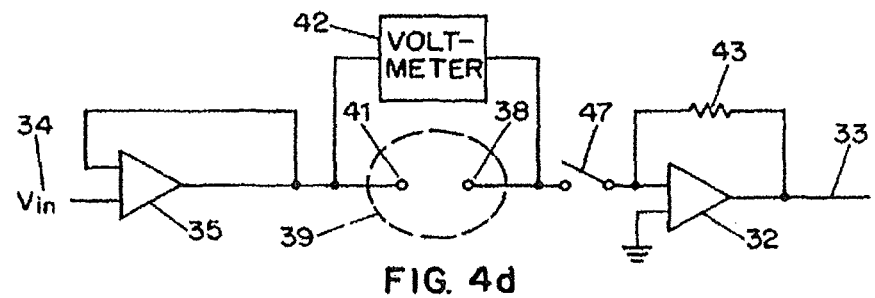

FIGS. 4c and 4d show embodiments in which one switch is used to effect the isolation. In each embodiment, a single switch is opened to isolate the cell for purposes of voltage measurement by means of voltmeter 42.

In FIG. 4c, switch 46 is opened to isolate the two-electrode cell 39 from the output of amplifier 35.

In FIG. 4d, switch 47 is opened to isolate the two-electrode cell 39 at the electrode 38.

In FIGS. 4a, 4b, 4c, and 4d, and indeed in many examples that follow, a single feedback resistor 43 is shown for simplicity, and is meant to represent the selector 31 and the current-range resistors 30.

Figure 1:
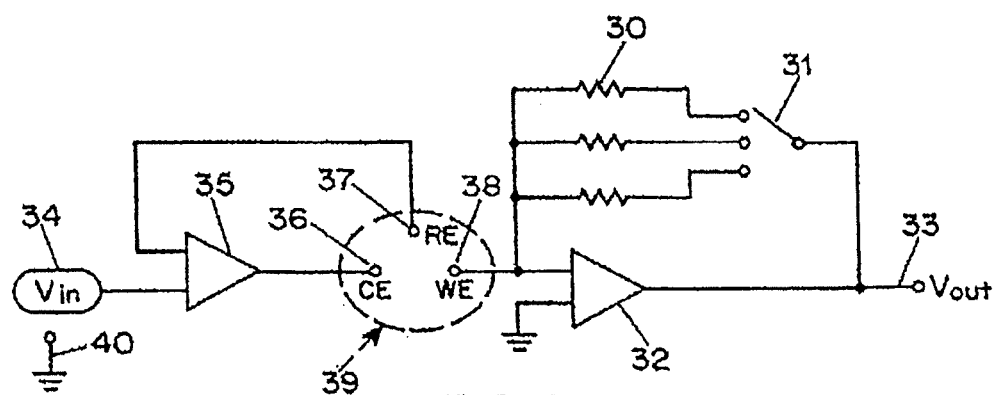
FIG. 1 is a schematic diagram of an electrochemical interface apparatus, also known as a potentiostat, for a standard three-electrode configuration.
Figure 2:
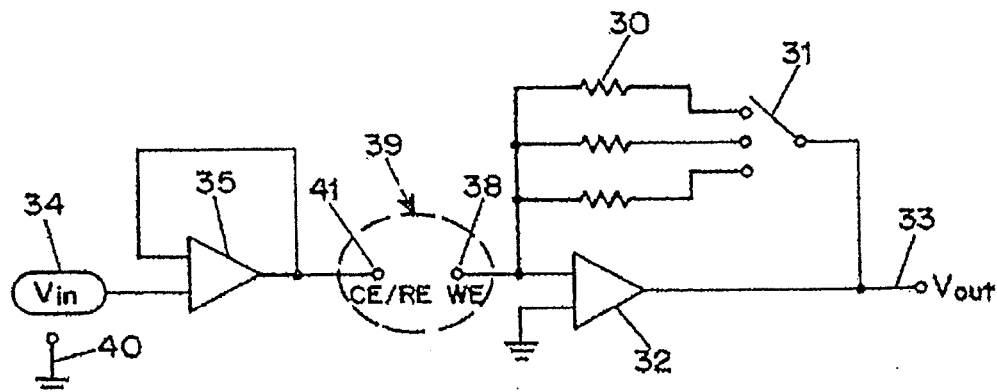
FIG. 2 shows an arrangement in which the counter electrode and the reference electrode are combined into a single electrode 41.
Figure 5A:
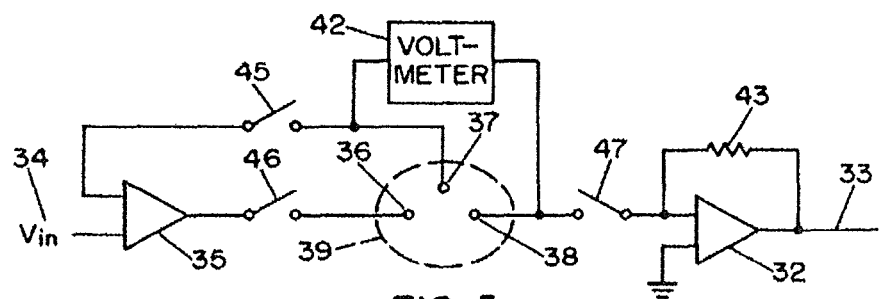
FIGS. 5a, 5b, and 5c show a three-electrode cell system in which it is possible to introduce voltage measurements by providing three switches.
Figure 5B:
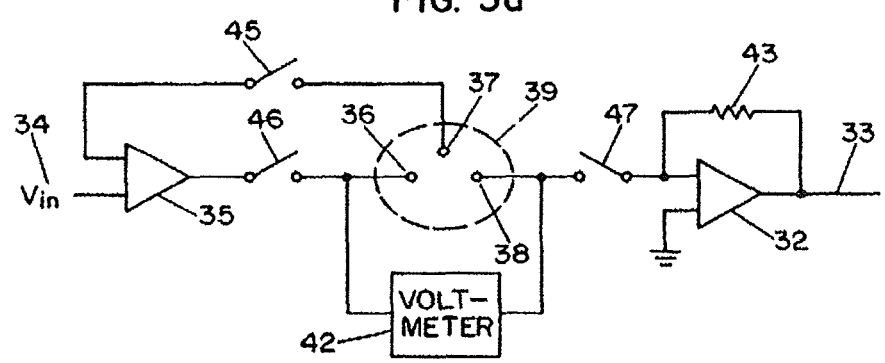
Figure 5C:
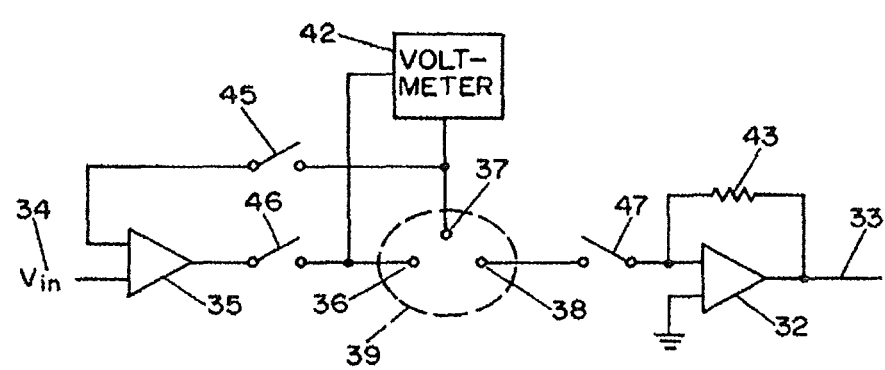

In a three-electrode cell system (see for example FIG. 1) it is possible to introduce voltage measurements by providing three switches, as shown in FIGS. 5a, 5b, and 5c. In each embodiment, switch 46 isolates the electrode 36 from the output of amplifier 35, switch 45 isolates the electrode 37 from the feedback path of amplifier 35, and switch 47 isolates the electrode 38 from the amperometric circuitry 32. In this way all three electrodes of the cell 39 are "floating" relative to other circuitry.

It is then possible to use a voltmeter to measure voltages. The voltage being measured is between the reference electrode 37 and the working electrode 38 (FIG. 5a), or between the counter electrode 36 and the working electrode 38 (FIG. 5b), or between the reference electrode 37 and the counter electrode 36 (FIG. 5c).

It will be appreciated that in some analytical applications, it may be desirable to measure more than one potential difference between electrodes of the cell.

Figure 6A:
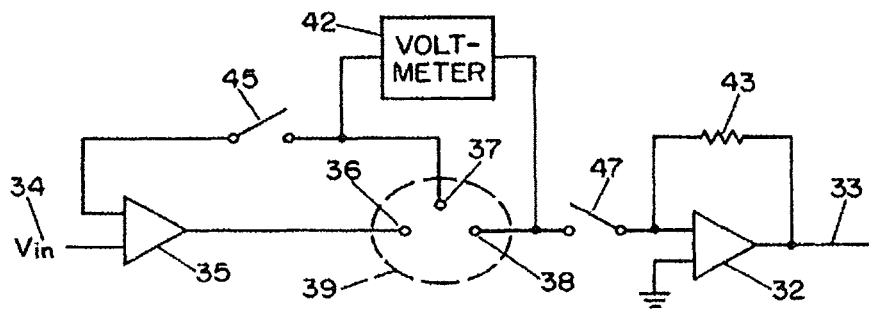
FIGS. 6a, 6b and 6c show a three-electrode cell system in which two switches are employed.
Figure 6B:
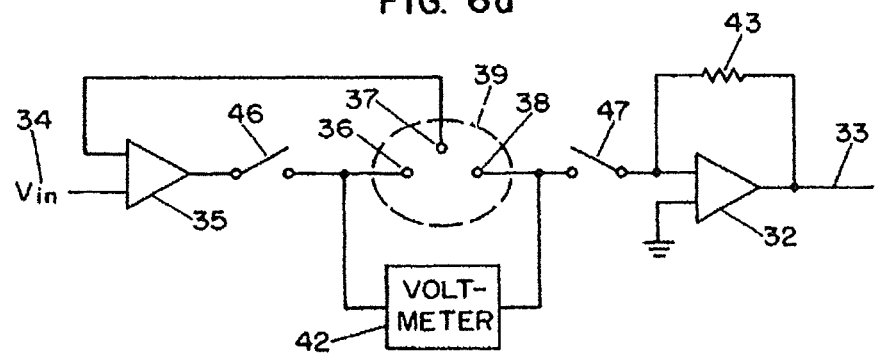
Figure 6C:
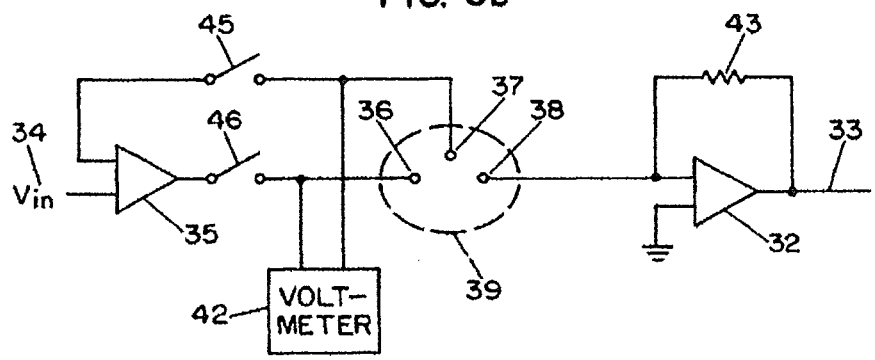

In a three-electrode cell system it is possible to introduce voltage measurements by providing two switches, as shown in FIGS. 6a, 6b, and 6c.

In FIGS. 6a and 6c, switch 45 isolates the electrode 37 from the feedback path of amplifier 35.

In FIGS. 6a and 6b, switch 47 isolates the electrode 38 from the amperometric circuitry 32.

In FIGS. 6b and 6c, switch 46 isolates the electrode 36 from the output of amplifier 35.

In this way two of the three electrodes of the cell 39 are "floating" relative to other circuitry.

It is then possible to use a voltmeter to measure voltages. The voltage being measured is between the reference electrode 37 and the working electrode 38 (FIG. 6a), or between the counter electrode 36 and the working electrode 38 (FIG. 6b), or between the reference electrode 37 and the counter electrode 36 (FIG. 6c). It should be borne in mind that such potential difference measurements may be made between any two points that are electrically equivalent to the two points of interest. Thus, for example, in FIG. 7a or 7b, the voltmeter 42, instead of being connected to electrode 38, could be connected instead to ground (which is one of the inputs of amplifier 32). This is so because the action of the amplifier 32 is such that the potential at 38 is forced to be at or very near the potential at the grounded input to the amplifier. In FIGS. 7c, 8a, and 8c, the voltmeter 42, instead of being connected to electrode 37, could be connected with the electrically equivalent (so far as potential is concerned) point 34.

Figure 7A:
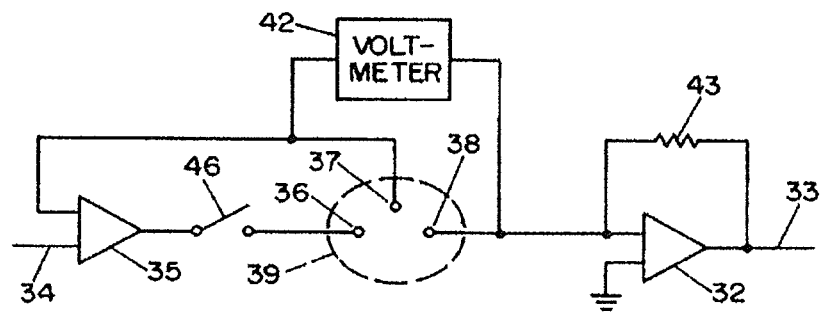
FIGS. 7a, 7b, and 7c show a three-electrode cell system in which it is possible to introduce voltage measurements by providing one switch.
Figure 7B:
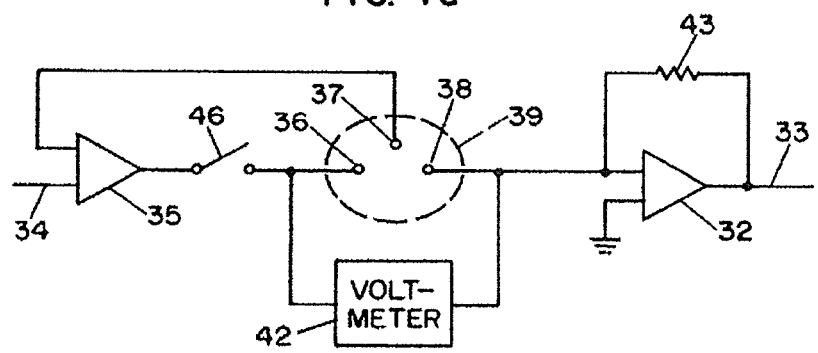
Figure 7C:
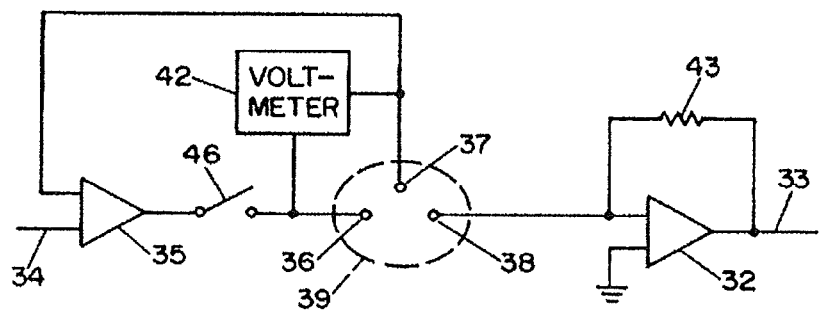
Figure 8A:
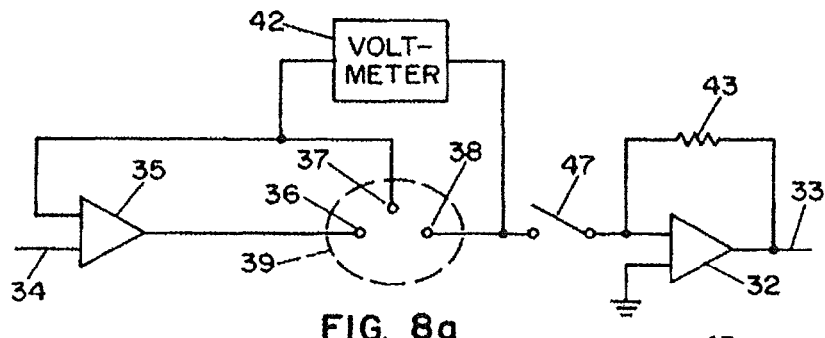
FIGS. 8a, 8b, and 8c show a three-electrode cell system in which another way is shown to introduce voltage measurements by providing one switch.

In a three-electrode cell system it is possible to introduce voltage measurements by providing one switch, as shown in FIGS. 7a, 7b, and 7c. In each case, switch 46 isolates the electrode 36 from the output of amplifier 35.

It is then possible to use a voltmeter to measure voltages. The voltage being measured is between the reference electrode 37 and the working electrode 38 (FIG. 7a), or between the counter electrode 36 and the working electrode 38 (FIG. 7b), or between the reference electrode 37 and the counter electrode 36 (FIG. 7c).

Figure 8B:
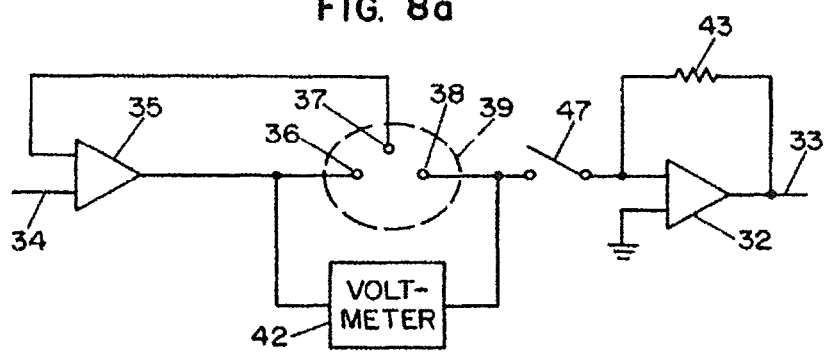
Figure 8C:
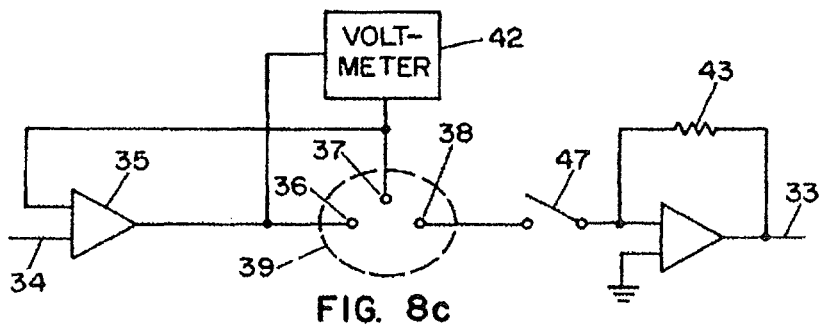

In a three-electrode cell system there is another way to introduce voltage measurements by providing one switch, as shown in FIGS. 8a, 8b, and 8c. In each case, switch 47 isolates the electrode 38 from the amperometric circuitry of amplifier 32.

It is then possible to use a voltmeter to measure voltages. The voltage being measured is between the reference electrode 37 and the working electrode 38 (FIG. 8a), or between the counter electrode 36 and the working electrode 38 (FIG. 8b), or between the reference electrode 37 and the counter electrode 36 (FIG. 8c).

It should also be appreciated that this approach can be generalized to cells with more than three electrodes.

Figure 10:
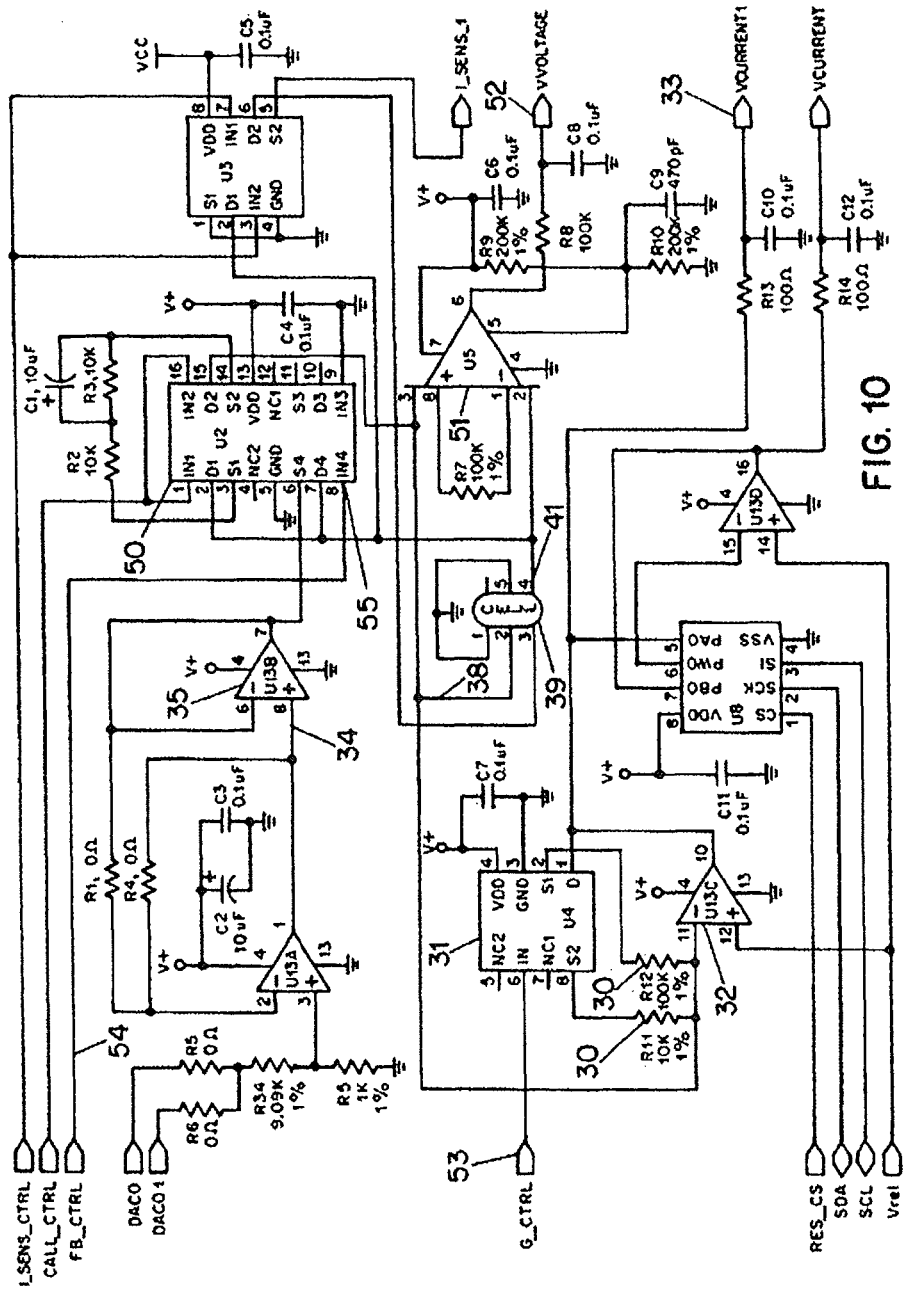
FIG. 10 shows an exemplary schematic diagram of a measurement system according to the invention, in greater detail than in the previous figures.

FIG. 10 shows an exemplary schematic diagram of a measurement system according to the invention, in greater detail than in the previous figures, and corresponding most closely to the embodiment of FIG. 3.

Resistor bank 30 may be seen, which together with selector 31 permits selecting feedback resistor values for amplifier 32. In this way the output at 33 is a voltage indicative of the current passing through working electrode 38. This corresponds to the amperometric circuitry of FIG. 3. Selector 31 in this embodiment is a single-pole double-throw switch with selectable sources S1, S2 and a destination D, controlled by control input IN, connected to control line 53.

Two-electrode cell 39 may be seen in FIG. 10, with electrode 41 serving as combined counter electrode and reference electrode.

Integrated circuit 50 of FIG. 10 contains four switches. One of the switches of circuit 50 is a switch 55 at pins 8, 6, 7 (input 4, source 4, and drain 4 respectively). This switch 55 corresponds to switch 44 in FIG. 3, and isolates the electrode 41 from the driver of amplifier 35. When the switch 55 is opened, it is possible to use amplifier 51 as a voltmeter, measuring the voltage between inverting pin 2 and noninverting pin 3, thereby measuring the voltage between the two electrodes 38, 41 of the cell 39. The voltage at output 52 is proportional to the voltage measured at the inputs of amplifier 51.

The opening and closing of the switch 55 is controlled by control line 54. (It should also be appreciated that with appropriate switching, as discussed below, it is possible to use a smaller number of amplifiers in a way that fulfills the roles of both the amperometric circuitry and the potentiometic circuitry.)

What is shown in FIG. 10 is thus a powerful and versatile analysis circuit that permits at some times measuring voltage across the electrodes of an electrochemical cell, and that permits at other times performing amperometric measurements across those same electrodes. This permits an automated means of switching between modes. In this way the apparatus differs from prior-art electrochemical analytic instruments which can operate in a potentiostat (amperometric) mode or in a galvanostat potentiometric mode, but which require a human operator to make a manual selection of one mode or the other.

In addition, it will be appreciated that the apparatus of FIG. 10 can also monitor voltage during an amperometric measurement if certain switches are closed. In other words, the amperometric and potentiometric measurements need not be at exclusive times.

It will also be appreciated that the switching between amperometric and potentiometric modes need not be at fixed and predetermined times, but can instead be performed dynamically depending upon predetermined criteria. For example a measurement could initially be an amperometric measurement, with the apparatus switching to potentiometric measurement after detection of some particular event in the course of the amperometric measurement.

Among the powerful approaches made possible by such a circuit is to use an amperometric mode to generate a chemical potential, which can then itself be measured by potentiometry.

Figure 13:
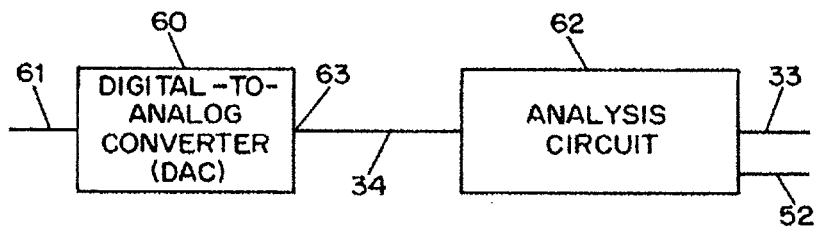
FIG. 13 shows a functional block 62 which can be the analysis circuit of any of the previously discussed figures.

Turning now to FIG. 13, what is shown is a functional block 62 which can be the analysis circuit of any of the previously discussed figures. A voltage input 34 may be seen as well as an output 33 indicative of current in an amperometric measurement. The functional block 62 may comprise a three-terminal reaction cell 39 or a two-terminal reaction cell 39 as described in connection with the previously discussed figures.

Optionally there may be a voltage output 52 indicative of voltage measured by a voltmeter 42, omitted for clarity in FIG. 13. In such a case, one or two or three switches (also omitted for clarity in FIG. 13) are used to isolate the cell 39 to permit potential (voltage) measurement.

Importantly in FIG. 13, input 34 is connected to a digital-to-analog converter (DAC) 60 which receives a digital input 61. In the most general case the DAC is a fast and accurate DAC, generating complex waveforms as a function of time at the output 63 which is in turn connected with the input 34 of the block 62.

In some cases it may turn out that the DAC can be a less expensive circuit. For example, it may turn out that it can be a simple resistor ladder connected to discrete outputs from a controller. As another example it may turn out that a pulse-width-modulated output from a controller can be used to charge or discharge a capacitor, giving rise to a desired output at 63 and thus an input at 34. Such a circuit may be seen for example in co-pending application Ser. No. 10/907, 806, which application is incorporated herein by reference for all purposes.

In this way it is possible to apply time-varying waveforms to reaction cells 39, for example ramps and sinusoids.

The benefits of the invention, for example the use of automatically controlled switching between amperometric and potentiometic modes, and the use of time-variant voltage inputs for the amperometric measurements, offer themselves not only for the glucose measurement mentioned above, but for myriad other measurements including blood chemistry and urine chemistry measurements, as well as immunoassays, cardiac monitoring, and coagulation analysis.

Figure 11:
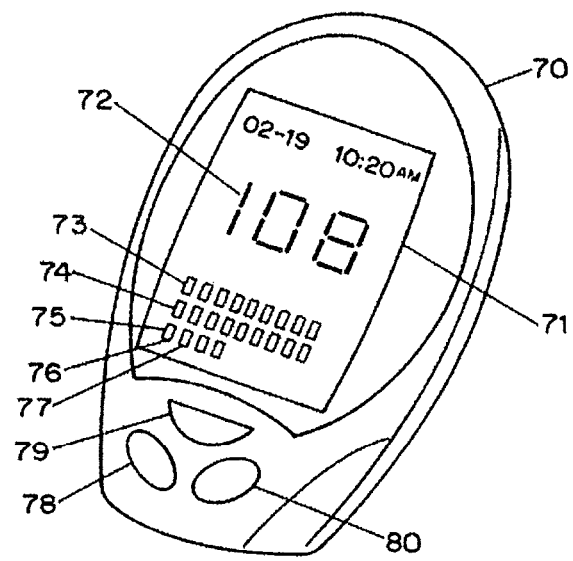
FIG. 11 is a perspective view of a test instrument 70.

Turning now to FIG. 11, what is shown is a perspective view of a test instrument 70. A display 71 provides information to a user, and pushbuttons 78, 79, 80 permit inputs by the user. Display 71 is preferably a liquid-crystal display but other technologies may also be employed. Large seven-segment digits 72 permit a large portrayal of an important number such as a blood glucose level.

Importantly, a rectangular array of low-resolution circles or other areas can show, in a rough way, qualitative information. This may include hematocrit level, a multi-day history trend graph, a filling rate, a temperature, a battery life, or memory/voice-message space remaining. The array can also be used to show "progress bars" which help the human user to appreciate that progress is being made in a particular analysis. The array may be fifteen circles wide and six rows high.

Thus one way to use the display is to show a very rough bar graph in which the horizontal axis represents the passage of time and in which the vertical axis represents a quantity of interest. For each time interval there may be none, one, two, or three, four, five, or six circles turned on, starting from the bottom of the array.

Another way to use the display is to show a very rough bar graph with between none and fifteen circles turned on, starting at the left edge of the array.

In this way, at minimal expense, a modest number of circles (in this case, ninety circles) may be used in a flexible way to show quantitative information in two different ways. The circles are preferably addressed individually by means of respective traces to a connector at an edge of the liquid-crystal display. Alternatively they may be addressed by row and column electrodes.

The number of circles in a row may be fifteen.

Figure 9:
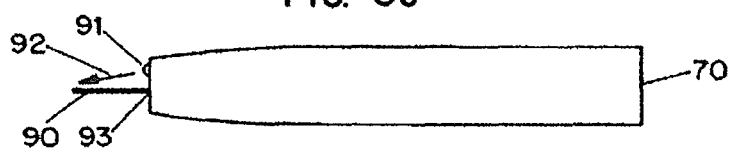
FIG. 9 is a test instrument 70 in side view.

Turning now to FIG. 9, what is shown is a test instrument 70 in side view. A test strip 90, containing an electrochemical cell 39 (omitted for clarity in FIG. 9), is inserted into the test instrument 70 by means of movement to the right in FIG. 9.

It will be appreciated that the user of the test instrument 70 may have difficulty inserting the test strip 90 into the instrument 70. This may happen because the user has limited hand-eye coordination or limited fine-motor control. Alternatively, this may happen because the user is in a place that is not well lit, for example while camping and at night. In either case, the user can benefit from a light-emitting diode (LED) 91 which is used to light up the area of the test strip 90. There is a connector 93 into which the strip 90 is inserted, and the LED 91 is preferably illuminated before the strip 90 is inserted.

In one prior art instrument there is an LED at a connector like the connector 93, but it only can be turned on after the strip like strip 90 is inserted. As such it is of no help in guiding the user in insertion of the strip.

Importantly, then, with the apparatus of FIG. 9, the user can illuminate the LED before inserting the strip. This may be done by pressing a button, for example. This may cast light along path 92, illuminating the tip of the strip. It may also cast light upon the connector 93, or both.

Figure 12:
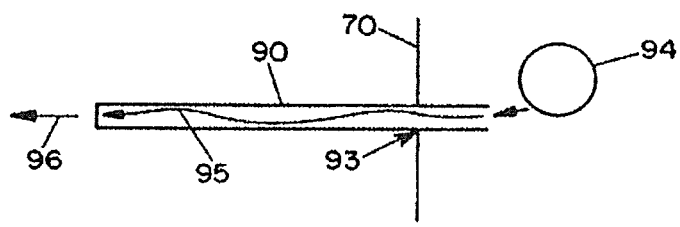
FIG. 12 shows a strip having the ability to serve as an optical waveguide.

It may also be helpful to illuminate the tip of the strip in a different way. The strip 90 as shown in FIG. 12 may have the ability (due to being partly or largely transparent) to serve as an optical waveguide. For example many adhesives usable in the manufacture of such strips are transparent. Light can pass along the length of the strip as shown at 95, emitted at the end as shown at 96. In this way it is possible to illuminate the lanced area (the area that has been pricked to produce a drop of blood) so that the tip of the strip 90 can be readily guided to the location of the drop of blood.

The light-transmitting section of the strip 90 may be substantially transparent, or may be fluorescent or phosphorescent, so that the strip lights up and is easy to see.

Experience with users permits selecting an LED color that is well suited to the task. For example a blue LED will offer very good contrast when the user is trying to find a drop of red blood, working better than a red LED.

Figure 14:
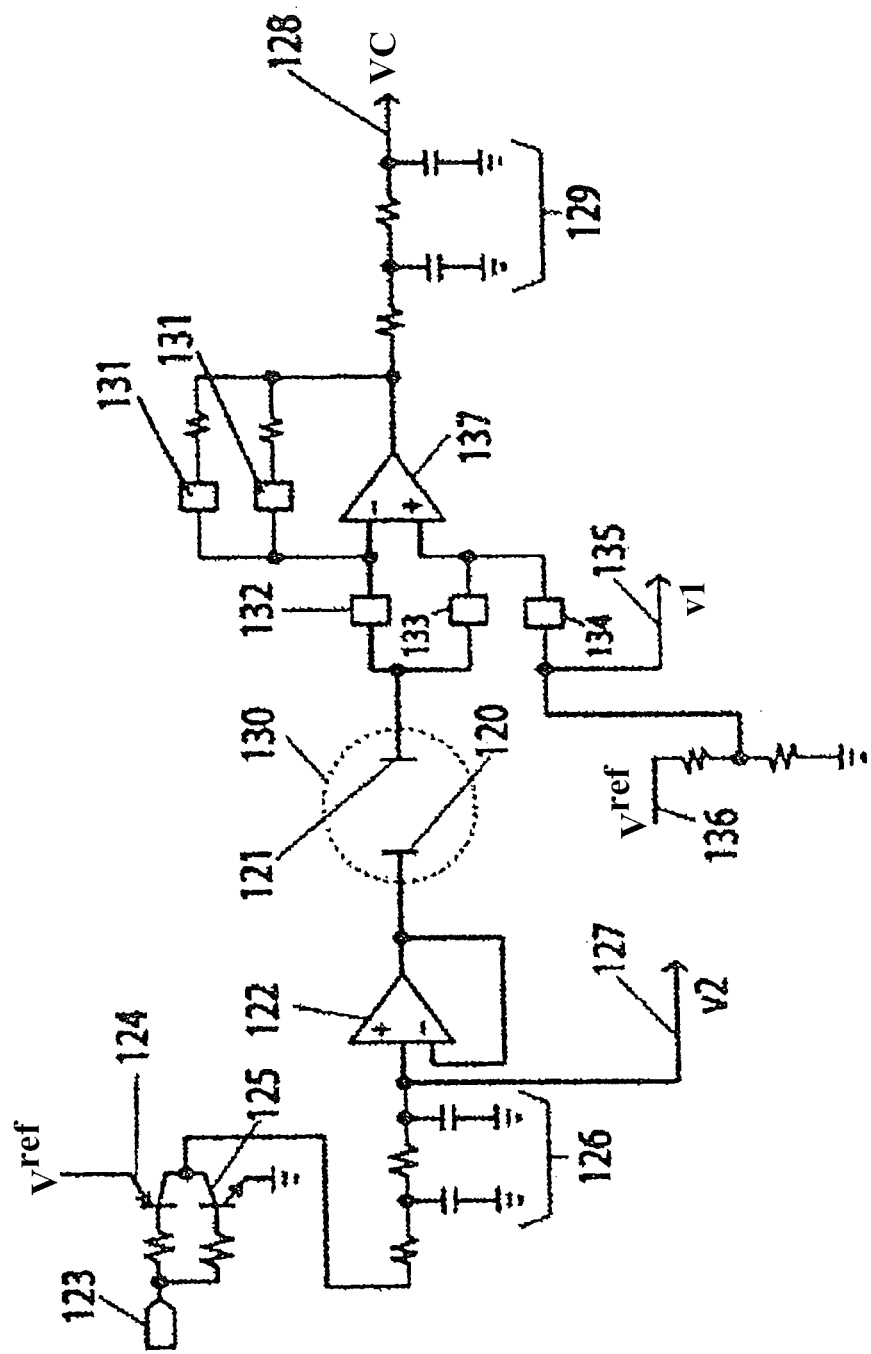
FIG. 14 shows how, with proper use of analog switches, the number of operational amplifiers may be reduced to as few as two.

Turning now to FIG. 14, a circuit requiring only two operational amplifiers 122, 137 is shown. Central to the circuit is reaction cell 130 having a working electrode 120 and a counter electrode 121. Operational amplifier 122 serves as a unity-gain amplifier (buffer) applying voltage V2 to the working electrode 120. Pulse-width-modulated control line 123 turns transistors 124, 125 on and off to develop some desired voltage through low-pass filter network 126. This developed voltage V2 is measured at line 127, which in a typical case goes to an analog-to-digital converter for example at a microcontroller, all omitted for clarity in FIG. 14.

The manner of operation of the pulse-width-modulated line 123 is described in more detail in copending application Ser. No. 10/907,806, entitled "Method and apparatus for providing stable voltage to analytical system", filed Apr. 15, 2005, which application is hereby incorporated herein by reference for all purposes.

During the amperometric phase of analysis, switch 133 is open and switches 134 and 132 are closed. A reference voltage VREF at 136 develops a voltage V1 (135) which is measured, preferably by means of an analog-to-digital converter omitted for clarity in FIG. 14. This voltage is provided to an input of amplifier 137, and defines the voltage presented to the electrode 121. The voltage developed at 128 is, during this phase, indicative of the current through the reaction cell 130.

During the potentiometric phase of analysis, switch 133 is closed and switches 134 and 132 are opened. In this way the potential at the electrode 121 is made available to the amplifier 137 and from there to the sense line 128. The voltage developed at line 128 is indicative of the voltage at the electrode 121, and the voltage at electrode 120 is defined by the voltage at 127, and in this way it is possible to measure the potential difference between the electrodes 120, 121.

Describing the apparatus differently, what is seen is an apparatus used with a reaction cell having a first electrode and a second electrode. A voltage source provides a controllable voltage to the first electrode and a voltage sensor senses voltage provided to the first electrode. An amplifier is coupled with the second electrode by way of a switch means. The switch means is switchable between first and second positions, the switch means in the first position disposing the amplifier to measure current through the second electrode, thereby measuring current through the reaction cell. The switch means in the second position disposes the amplifier to measure voltage present at the second electrode. The switch means in an exemplary embodiment comprises first, second, and third analog switches, the first analog switch connecting the second electrode and an inverting input of the amplifier, the second analog switch connecting the second electrode and a non-inverting input of the amplifier, the third analog switch connecting the non-inverting input of the amplifier and a reference voltage. The first position is defined by the first and third switches being closed and the second switch being open, while the second position is defined by the first and third switches being open and the second switch being closed.

Returning to FIG. 14, a low-pass filter 129 is provided to smooth the signal at line 128.

It will be appreciated that if amplifiers suitable for use in this analysis are expensive, and if analog switches suitable for use at 132, 133, 134 are inexpensive, then it is desirable to employ a circuit such as is shown here to permit minimizing the number of amplifiers needed.

Those skilled in the art will have no difficulty devising myriad obvious improvements and variations upon the embodiments of the invention without departing from the invention, all of which are intended to be encompassed by the claims which follow.

What is claimed is:

1. An apparatus for use with a reaction cell having a first electrode and a second electrode, the apparatus comprising:
   a voltage or current source providing a controllable voltage or current to the first electrode;
   a voltage sensor sensing voltage provided at the first electrode;
   an amplifier;
   switch means switchable between first and second positions, said switch means in said first position disposing the amplifier to measure current through the second electrode, thereby measuring current through the reaction cell, said switch means in said second position disposing the amplifier to measure voltage present at the second electrode.

2. The apparatus of claim 1, wherein the switch means comprises first, second, and third analog switches, the first analog switch connecting the second electrode and an inverting input of the amplifier, the second analog switch connecting the second electrode and a non-inverting input of the amplifier, the third analog switch connecting the non-inverting input of the amplifier and a reference voltage, the first position defined by the first and third switches being closed and the second switch being open, the second position defined by the first and third switches being open and the second switch being closed.

3. A method for use in a test equipment apparatus having an electrochemical cell disposed to receive a bodily fluid of a human user, the apparatus comprising electronic circuitry, the method comprising the steps of:
   under automatic control of the electronic circuitry, allowing electrical current to flow through the cell by means of a current source or source of potential external to the cell and measuring said current;

thereafter, under automatic control of the electronic circuitry, ceasing the flow of electrical current from the current source or source of potential external to the cell; thereafter, under automatic control of the electronic circuitry, measuring an electrical potential at the cell; and evaluating a function of the measured current and the measured electrical potential, whereby a measure of characteristic of the bodily fluid is evaluated.

4. The method of claim 3 wherein the bodily fluid is blood.

5. The method of claim 4 wherein the electrochemical cell comprises a reagent reactive with glucose, and the evaluated characteristic of the blood is a concentration of glucose in the blood.

6. The method of claim 3 wherein the bodily fluid is urine.

7. The method of claim 3 wherein the measurement of the current comprises measuring the duration of the current.

8. The method of claim 3 wherein the allowing of electrical current to flow through the cell comprises applying a constant current through the cell.

9. The method of claim 3 wherein the allowing of electrical current to flow through the cell comprises applying a time-variant voltage to the cell.

10. The method of claim 9 wherein the voltage applied to the cell comprises a sinusoidal potential.

11. The method of claim 9 wherein the voltage applied to the cell comprises a ramp potential.

12. The method of claim 3 wherein the test equipment comprises a housing and the electrochemical cell is within a test strip external to the housing, the method further comprising the steps, performed before the step of allowing of electrical current to flow through the cell, of:

inserting the test strip into a connector at the housing, and applying the bodily fluid to the electrochemical cell.

13. The method of claim 12 further comprising the step, performed after the step of measuring an electrical potential at the cell, of:

removing the test strip from the housing.

14. The method of claim 3 wherein the electrochemical cell comprises at least first and second electrodes, and wherein the step of ceasing the allowing of electrical current to flow from the current source or source of potential external to the cell further comprises: opening a first switch whereby at least the first electrode of the electrochemical cell is isolated from the current source or source of potential external to the cell.

15. The method of claim 14 wherein the step of ceasing the allowing of electrical current to flow from the current source or source of potential external to the cell further comprises:

opening a second switch whereby at least the second electrode of the electrochemical cell is isolated from the current source or source of potential external to the cell.

* * * * *